United States Patent [19]
Neff

[11] 4,019,459
[45] Apr. 26, 1977

[54] AMPHIBIAN CULTURE BY INSECT FEEDING

[76] Inventor: Gregor N. Neff, 85 Myrtle Ave., Dobbs Ferry, N.Y. 10522

[22] Filed: Feb. 20, 1976

[21] Appl. No.: 659,690

Related U.S. Application Data

[60] Division of Ser. No. 477,839, June 10, 1974, abandoned, which is a continuation-in-part of Ser. No. 460,619, April 12, 1974, Pat. No. 3,939,802, which is a continuation-in-part of Ser. No. 213,966, Dec. 30, 1971, abandoned.

[52] U.S. Cl. .................................. 119/3; 119/51 R
[51] Int. Cl.² ........................................ A01K 67/00
[58] Field of Search ............... 119/51 R, 3; 43/100, 43/104, 113, 139

[56] References Cited
UNITED STATES PATENTS

| | | | |
|---|---|---|---|
| 2,126,056 | 8/1938 | Stearns | 119/51 R |
| 2,441,015 | 5/1948 | Fisher | 43/104 |
| 2,883,790 | 4/1959 | Blackman | 43/113 |

Primary Examiner—Hugh R. Chamblee
Attorney, Agent, or Firm—Curtis, Morris & Safford

[57] ABSTRACT

In the culture of confined aquatic animals such as fish, tadpoles and frogs, the cage or other confining structure is used both to restrain the animal being cultures, and also to trap wild aquatic animals (e.g. fish) for the animals being cultured to eat. Thus, a simple, low-cost automatic means is provided for supplementing the diet of insects, commercial food pellets, etc. which also is fed to the animals being cultured. The cage walls have a mesh size small enough to keep out all but the small aquatic animals. At least one fish-trap entrance structure is built into the walls of the cage. The entrance opening of the fish-trap structure is of a size such that only forage fish significantly smaller than the animals being cultured in the cage can enter, and the cultured animals cannot escape. The fish-trap structure substantially prevents escape of the forage fish until they have been eaten. Wild aquatic animals too large for use as forage are kept out of the cage so that they do not compete with the cultured animals for space and oxygen, and do not waste food. An expandable cage is provided with removable partitions. Forage animals are trapped and/or raised in some of the compartments. The partitions are removed as the cultured animals grow, thus expanding the living space and exposing the forage animals to be eaten by the cultured animals. Pond culture using net barriers and trap entrances to perform the feeding method also are described. Alternatively, separate cages with removable end partitions can be attached together to increase the living space for the animals. The culture of frogs or fish by feeding insects into an enclosure such as a covered tank on land also is described. Insect traps disclosed include one using air downdrafts and linear blacklight bulbs. Another uses a translucent screen, a blacklight, and a funnel-shaped hopper to catch insects falling off the screen.

8 Claims, 10 Drawing Figures

U.S. Patent   April 26, 1977   Sheet 1 of 3   4,019,459
FIG. 1
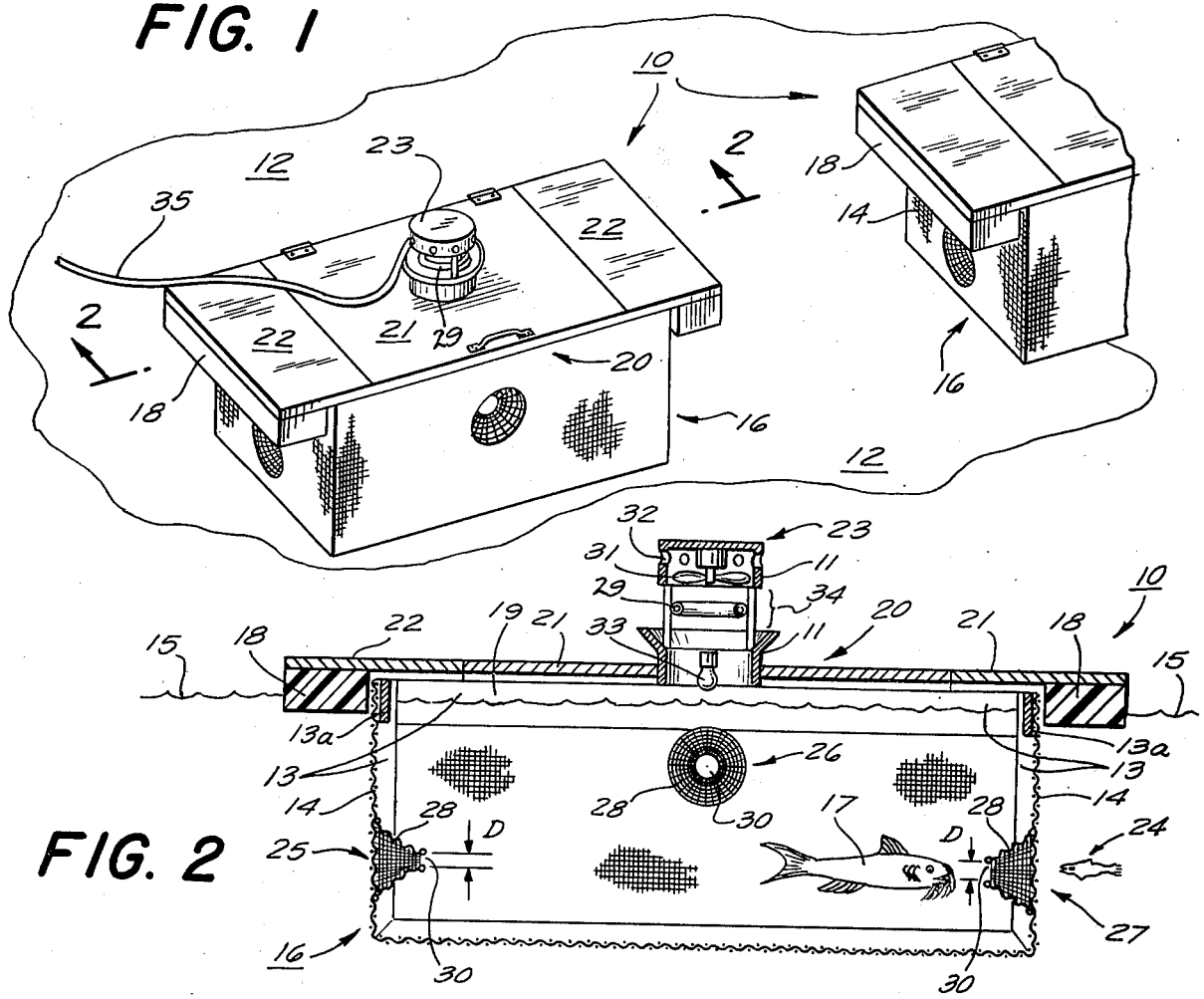
FIG. 2
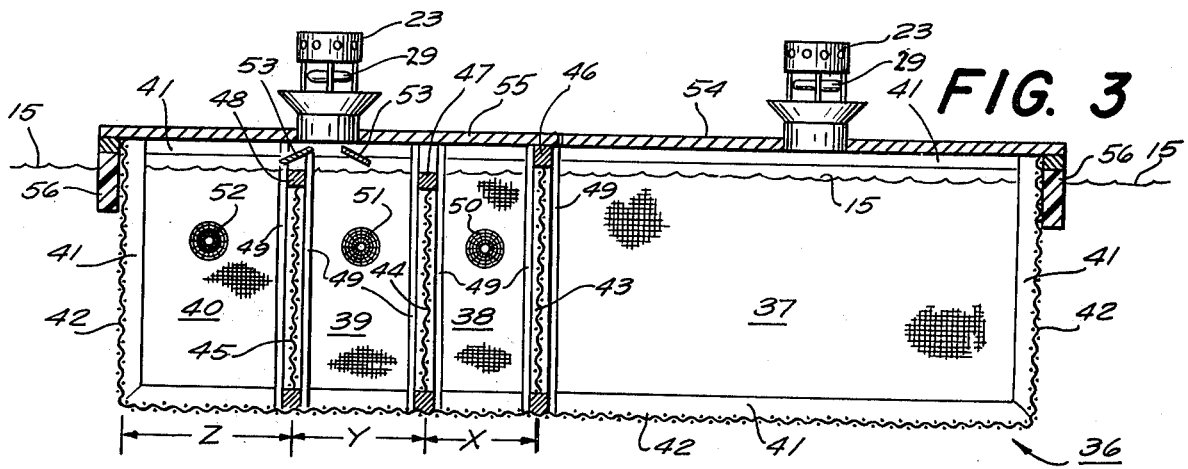
FIG. 3
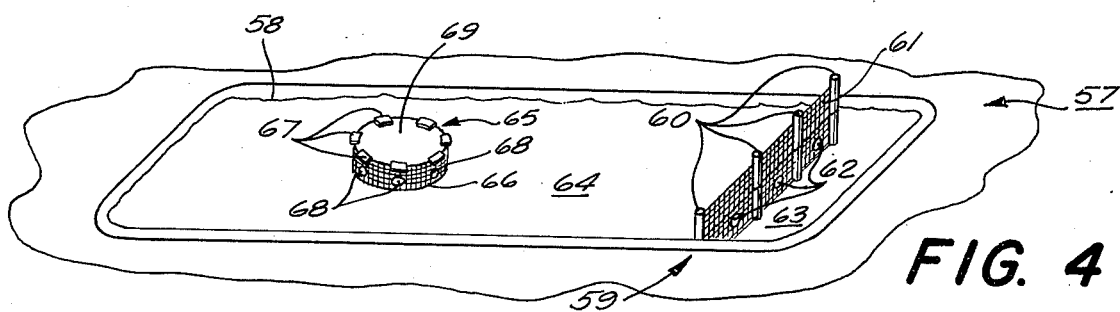
FIG. 4

AMPHIBIAN CULTURE BY INSECT FEEDING

This invention relates to aquaculture; more particularly, this invention relates to the rearing of confined aquatic animals, such as fish, frogs, shrimp, etc. in enclosures. This application is a division of application Ser. No. 477,839, filed June 10, 1974, now abandoned, which is a continuation-in-part of my co-pending U.S. patent application Ser. No. 460,619, filed Apr. 12, 1974, now U.S. Pat. No. 3,939,802, which is a continuation in part of Ser. No. 213,966, filed Dec. 30, 1971, now abandoned. The disclosures of those applications hereby are incorporated herein by reference.

Aquaculture is and long has been plagued by the high cost of feed and the high cost of labor required in feeding aquatic animals which are being raised. For this reason, the price of aquaculture products such as fish, frogs, shrimp, etc. are believed to be higher than they need be.

The culture of aquatic creatures confined in structures such as cages or tanks long has been attractive because it saves or more fully utilizes valuable land. For example, the cage culture of fish permits the use of large natural bodies of water for raising the fish, whereas pond culture methods usually require the expense of building ponds, and often take out of production substantial amounts of farmland which also could be used to advantage in growing row crops such as soy beans, corn, rice, wheat, etc. However, the high cost of feed and labor exists in confined culture as well as pond culture. Furthermore, the advantages of confined culture must be weighed against the cost of the confining structures. For these reasons, it is believed, confined culture has not gained the commercial acceptance that it might have.

In accordance with the foregoing, it is an object of the invention to reduce the cost of the confined culture of aquatic animals. It is a more specific object to reduce the cost of food and labor required in the confined culture of aquatic animals. It is another object of the invention to provide such improvements in the use of floating cages in the culture of aquatic animals. It is also desired to provide better foods for the growth of aquatic animals. Furthermore, it is an object to incrase the effective utilization of cages in cage culture, and thereby lower the cost of providing cages. It is an object to do this while minimizing the extra handling, labor costs and trauma to the animals.

In accordance with the present invention, the foregoing objects are met by the provisions of a method and device for the culture of confined aquatic animals in which other aquatic animals from the water surrounding the confining structure are trapped in the confining structure and used as forage for the animals being reared. The aquatic animals are trapped in the confining structure either alone or with insects, with the insects serving as food for the animals being cultured. Insects alone also can be trapped in the structure. The forage animals preferably are attracted into the enclosure by means of the food fed to the animals being reared. This food can consist of commercial food pellets, or insects captured in insect traps and/or other food items attractive to the forage animals. In the preferred embodiment, the invention is described in use in a system for feeding fish, tadpoles or frogs in cages immersed in natural waterways such as canals, lakes, etc. in which there are substantial quantities of wild forage animals such as minnows, shiners, chubs, mosquito fish, etc. The frogs also are fed insects by trapping the insects in the same enclosure with the frogs. The feeding of aquatic animals on land or water by enclosing them and insects in the same enclosure also is described. The cage culture of aquatic animals is facilitated by providing expandable cages. Thus, the cages can be used to near capacity at all times.

The foregoing and other objects, advantages and features of the invention will be set forth in or apparent from the following description and drawings. In the drawings:

FIG. 1 is a perspective view illustrating the preferred embodiment of the present invention;

FIG. 2 is a cross-sectional view taken along line 2—2 of FIG. 1;

FIG. 3 is a cross-sectional view of an alternative embodiment of the invention;

FIG. 4 is a perspective view of other alternative embodiments of the invention;

Figure 5:
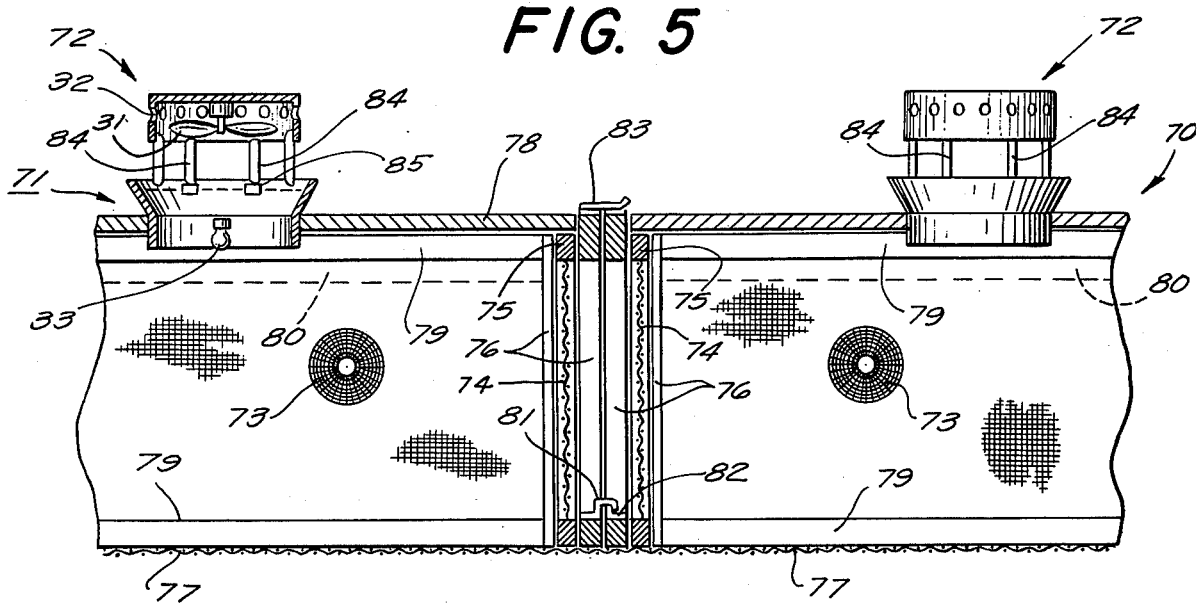
FIGS. 5 and 6 are cross-sectional views of alternative embodiments of the invention.

FIG. 1 shows a plurality of fish cages 10 partially immersed in a large body of water 12 such as a lake, canal, river, etc. Each of the cages includes a frame 13 (see FIG. 2), mesh enclosure material 14, such as wire mesh coated with protective agents, or plastic screen or mesh. The frame and mesh forms a fish enclosure 16 beneath the surface 15 of the water. Within the enclosure 16 thus formed are retained a substantial number of fish 17 such as channel catfish, trout, etc. to be reared.

The cage 10 includes flotation material such as styrofoam 18 to float the cage on the surface of the water. A cover 20 covers the top of the cage. The cover 20 includes a central hinged portion 21 and side portions 22. If desired, the cage can be left open.

An insect trap 23 is mounted over an opening in the control portion 21 of the cover 20. The insect trap is used to lure forage fish and other aquatic animals into the cage enclosure 16.

Outside of the cage enclosure 16 and within the body of water 12 are a plurality of small wild fish 24 which occur naturally in the body of water. These wild fish can be minnows, shiners, mosquito fish, small sunfish or bluegills, perch, etc.

In accordance with one aspect of the invention, several fish-trap entrances 25, 26 and 27 are provided in the walls of the cage 10 below the water-line 15. Each such entrance includes a frusto-conically shaped wall 28 with an opening 30 at the inner end. The cone faces inwardly toward the interior of the cage.

Still referring to FIG. 2 as well as FIG. 1, the diameter or smallest dimension D of the opening 30 is made large enough to allow the small fish to enter the cage, but too small to allow the fish being reared to escape from the cage. When the wild fish enter the cage through the openings 30, because of the inverted conical shape of the entrance, they cannot easily find their way out, and are trapped within the cage enclosure 16.

Thus, the fish being raised in the cage can eat the incoming fish as forage to increase their growth. This source of forage fish costs nothing and will reduce the amount of commercial or other feed which must be fed to the fish.

The size D of the opening 30 should be such that the forage fish allowed to enter are substantially smaller than the fish being raised so as to ensure that the forage fish will be eaten and will not eat a large amount of the food provided in the cages for the fish being reared. The mesh size of the cage mesh 14 should be significantly smaller than the entrance size D and small enough to prevent all but the very smallest aquatic animals from entering the enclosure 16.

Bait should be provided for attracting forage fish into the cages. Advantageously, the food which is fed to the fish being cultured also serves as bait to attract the forage fish. For example, floating pellets of fish food which are sold as fish feed can be used. Sinking fish food pellets can be used when held in a submerged tray or pan in the cages. The devices and methods described in my above-identified prior patent applications can be used to feed insects to the cultured fish, and the insects serve as bait for the forage fish as well as food for the cultured fish.

The insect trap 23 (see FIGS. 1 and 2) is provided for attracting and feeding insects into the air space 19 (see FIG. 2) between the cover 20 of the cage and the water surface 15. The insect trap 23 includes a housing 11 with an opening 34 separating the housing into upper and lower halves. A circular "blacklight" electric lamp 29 is mounted in the housing 11 near the opening 34 so that light from the lamp 29 can be seen by insects flying in the vicinity of the cage 10. An electric fan 31 is mounted in the upper part of the housing so as to create a downwardly-directed draft of air over the lamp 29. The blades of the fan extend considerably beyond the outline of the lamp so as to ensure that the air draft will blow substantially all of the insects attracted to the lamp 29 down into the lower part of the housing 11 and into the cage 10. The upper edge of the lower portion of the housing 11 is flared outwardly in order to catch more of the air and insects being blown downwardly. The air draft urges the insects into the water where they can be eaten by the fish. A strip 13a of material extends around the upper inside perimeter of the cage to serve as a retaining ring to hold insects and other food in the cage.

A small electric lamp 33 is positioned in the lower part of the housing 11 in order to provide white light to attract the fish 17 and 24 to the insects and encourage them to eat. This lamp 33 is provided if the fish 17 and 24 either are repelled by the predominantly ultraviolet light from the lamp 28, or are not induced to feed by the light from the lamp 29. Also the white light is known to attract small fish. Thus, it can be used, either alone or in conjunction with the insect trap 23, to attract forage fish into the cage 10.

Electric power for the fan and lamps is supplied over a cable 35 (FIG. 1) from a portable or other generator, or from conventional public power sources.

FIG. 3 of the drawings shows an embodiment of the invention in which forage fish are trapped in cage portions 38, 39 and 40 which initially are separate from the portion 37 in which fish are cultured, but later are made accessible to the cultured fish. Thus, the living room of the cultured fish in the cage 36 is expanded, and they are fed forage fish at the same time.

The cage 36 shown in FIG. 3 includes a frame 41 with an outer mesh enclosure 42 of a mesh size small enough to keep large forage fish out and small fingerling cultured fish in the cage. The four compartments 37, 38, 39 and 40 are formed by partitions consisting of removable screens 43, 44 and 45 mounted in frames 46, 47 and 48, respectively. The frames are slidably mounted in vertical guides 49 so that they can be removed by lifting them upwardly out of the cage.

Each of the compartments 38, 39 and 40 has a frusto-conical fish-trap entrance 50, 51 or 52, respectively, through which forage fish can enter. Two insect traps 23 are provided, one being mounted on a hinged cover 54 for the compartment 37, and the other on another hinged cover 55 over the other compartments. The insect trap for the smaller compartments has baffles 53 for distributing the insects to the compartments. A space is left between the baffles 53 so that some of the insects are blown straight down into the compartment 39, as well as to both sides. The partition 43 extends up to the cover 55, whereas the partitions 44 and 45 do not. This separates the air spaces above the compartments 38–40 from that above the compartment 37. However, if a single insect trap 23 is used to feed insects to all compartments, then the partition 43 will stop at the surface of the water rather than extend to the cover 55. A food-retaining and flotation ring is formed by a strip 56 of styrofoam extending around the cage at its upper edge.

The spacings of the partitions from one another and from the left end wall of the cage are indicated by the letters X, Y and Z. The distance Y is greater than X, and Z is greater than Y, thus making the volume of compartment 39 greater than that of compartment 38, and 40 greater than 39.

When the cage 36 first is put into use, fingerlings are placed in the compartment 37 at nearly full capacity; a density which is greater than that at which marketable-size fish could be reared effectively. At the same time, small forage fish are trapped from the surrounding water in the compartments 38–40. It is presumed that the culture fish are too small to eat forage fish at first. If not, then fish-trap entrances with small entrance diameters can be placed in the walls of the compartment 37 to admit forage fish immediately.

When the cultured fish have grown to a size such that they need more living space, they also will be large enough to eat the forage fish. At this time, the cover 55 is raised and partition 43 is lifted out, exposing the forage fish trapped in compartment 38 to the cultured fish, so that the living space of the cultured fish is increased at the same time as the forage fish are fed to the cultured fish.

Later, when the cultured fish have grown larger, the second partition 44 is removed. This enlarges the cage even more and feeds the cultured fish even more forage fish of a larger size than when the first partition 43 was raised. The forage fish are larger, on the average, because they have been fed and have grown while being trapped.

The process is repeated later when the third partition 45 is removed. The size of the resulting cage should be adequate to house all of the market-size fish originally placed in the cage.

As the partitions 43–45 are removed, the food supply to the cultured fish is increased, not only by the number of forage fish fed from one of the compartments 38–40, but also because a portion of the insects from the second insect trap 23 now is supplied to the cultured fish. Also, the fish-trap entrances 50–52 are progressively exposed to the cultured fish so that progressively greater members of forage fish are made available through those entrances. Thus, the living space and the food supply facilities are gradually expanded as the fish grow, without moving the fish from one cage to another, and without commensurate increases in the amounts of supplemental feed required. The feeding of insects to the forage fish causes them to grow, thus storing some of the feed value of the insects in the forage fish. This is one method of storing the food value of insects for use as feed during portions of the year when insects are not abundant; the fattened forage fish are fed instead.

FIG. 5 shows another embodiment of the expandable cage concept embodied in the cage of FIG. 3. In this embodiment two or more cages 70 and 71 can be attached to one another in order to expand the living space of fish growing in one of the cages 70. The other cage 71 can contain forage fish, or can be empty. Preferably, each cage has its own insect feeder 72 and fish-trap entrance 73.

At least one end wall of each cage consists of a removable screen partition 74 in a frame 75 which is adapted to slide vertically in a track formed by vertical guide members 76. Hook members 81 and 82 at the bottom and two latches 83 (only one is shown) at the top, are used in order to fasten the cages 70 and 71 together.

Each cage has a frame 79, of which the guide members 76 form a part, a hinged cover 78 and an outer mesh covering 77.

Flotation material 80 forming a feed-retaining ring is on the outside of the cage, except at the end where the partition is located; there the flotation material is on the inside of the partition so as not to interfere with the joining of the cages.

After the cages have been fastened together as shown in FIG. 5, the covers 78 are raised and the partitions 74 are removed so as to give the fish in cage 70 free access to the cage 71 and any forage fish it may contain.

The insect feeders 72 are the same as the feeder 23 shown in FIG. 2, except that two or more linear "blacklight" fluorescent bulbs 84 are used instead of the circular bulb 29. Sockets and a large mesh screen 85 are shown schematically for supporting the bulbs 84 vertically. The slim profile of each bulb 84 reduces the side-deflection of the downdraft from the fan 31 and improves the collection of insects.

FIG. 4 shows other types of means for confining fish to be cultured in a larger body of water. Shown in FIG. 4 is a rectangular pond 57 with a water line 58. A fish barrier 59 is formed across the bond by a plurality of posts driven into the bottom of the pond and a fine-mesh net 61 fastened to the posts and extending from the pond bottom to above the water surface. Fish trap entrances 62 are formed in the net 61 to allow small forage fish to enter either the area 64 to the left of the net or area 63 to the right, depending upon which area the cultured fish are being reared in. The net 61 can be used first as a siene to rid one of the areas 63 or 64 of forage fish, and then cultured fish can be put into the cleaned-out area. The fish-trap entrances 62 are directed so as to guide small forage fish into the cleaned-out area, and exclude larger forage fish which would waste food and oxygen needed for the cultured fish.

Another form of confining means shown in FIG. 4 is a ring 65 formed by a floating net 66 with floats 67. The net 66 touches the bottom of the pond. The net has fish-trap entrances 68. Either the cultured fish or the forage fish are trapped within the ring area 69, and forage fish are trapped in the remaining water with the cultured fish, as with the barrier 59.

The openings 30 in the fish trap entrances preferably are formed by rings made of ductile, corrosion-resistant material such as aluminum. This enables the dimension D of the openings to be made small initially and to be enlarged as the fish being reared grow larger. Thus, while the cultured fish are small, the forage fish trapped in the cage are limited to a small size. When the cultured fish grow larger, larger forage fish are admitted so as to increase the usable range of sizes for the forage fish. The size of the opening can be reduced by compressing the ring into an oval or elliptical shape, and is enlarged by restoring it towards a circular shape.

The fish being cultured in the area 63 or 64 or 69 can be fed commercial foods, and they can be fed insects by means of floating feeders of the variety shown in my above-identified co-pending patent application.

The aquatic animals being reared can include not only fish, but also frogs, tadpoles, shrimp, crawfish, lobsters, crabs, etc. The aquatic animals used as forage include any which are edible by the animals being raised, and which can be enticed into the cages. Such forage animals can include fish, shrimp, crawfish, insect larvae, adult water insects, tadpoles, frogs, etc.

Figure 6:
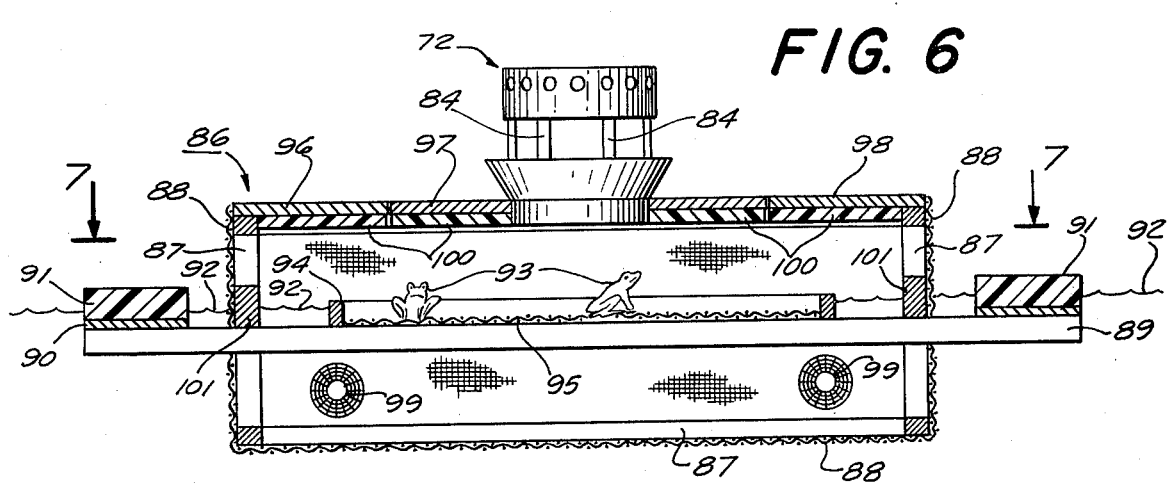
Figure 7:
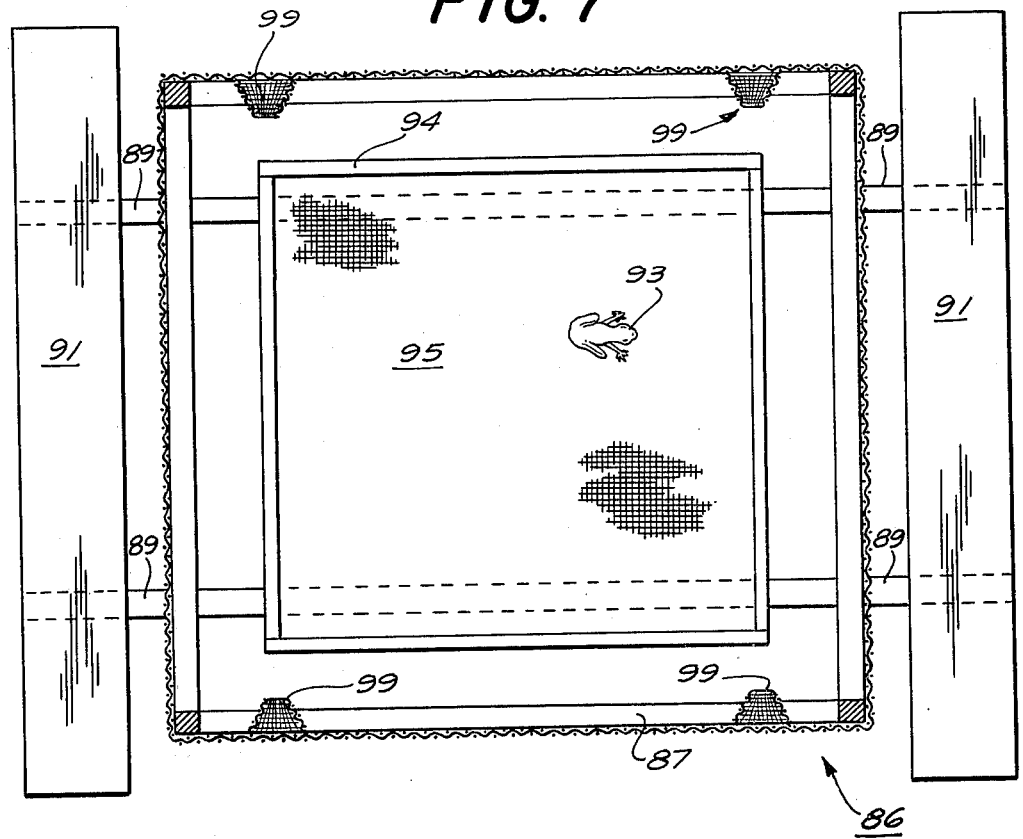
FIG. 7 is a cross-sectional view taken along line 7—7 of FIG. 6.

FIGS. 6 and 7 show an embodiment of the invention for use in frog culture. A floating cage 86 is used. The cage has a frame 87 covered on the bottom and four sides with plastic screen 88 which has a mesh size small enough to hold small insects in the cage. The top is covered by three hinged covers 96, 97 and 98.

Two cross-members 101 rest on two float support members 89 which extend out of the cage and support two broad, flat plastic foam floats 91 secured to support planks 90. The floats are spaced outwardly from the cage, and extend beyond the cage outline at each end (see FIG. 7) in order to minimize tipping of the cage.

An insect feeder 72 identical to the feeder shown in FIG. 5 is mounted in the cover 97. A frog support platform consisting of a frame 94 and screen 95, or a sheet of perforated fiberboard, is located below the insect feeder 72 so that the frogs easily can eat insects blown downwardly by the feeder 72. Fish trap entrances 99 are located in the cage wall below the level of the frog platform. Foam rubber pads 100 line the inside of the covers to protect the frogs from injury if they hit the covers when they jump.

The floats 91 are made considerably larger than they need be to support the weight of the cage and frogs. The purpose of this is to hold the cage at approximately the same position relative to the water line 92 despite changes in the weight of the frogs or shifting of the frogs in the cage. This position is one in which the platform bottom is covered with from ½ to 2 inches of water.

The edges of the frog platform are spaced by a considerable distance from the cage walls so as to provide space for the frogs to dive into the surrounding water. The frogs can swim in the areas around and under the platform, where they can capture and eat minnows and other small aquatic animals trapped in the cage by means of the trap entrances 99.

The frog platform has an upstanding lip or flange 94 formed by the frame 94. This helps retain any minnows, insects or other food which might be deposited on the platform for the frogs to eat. Alternatively, the flange can be omitted in order to permit the frogs to climb on and off the platform more easily.

The cage 86 is of square cross-section (see FIG. 7) as is the platform. It is believed that frogs will not bunch up in the corners because the corners are in the water. However, if the frogs do bunch up, the cage 86 can be given a circular shape, as can the platform. An alternative shape for the platform is a ledge extending around the periphery of the round cage, with a hole in the middle for the frogs to swim in.

If desired, frogs can be raised in the cage 86 from the egg or tadpole stage to full size, without the need for the traditional hatching and tadpole rearing pond. The frog platform can be removed until the tadpoles have changed into frogs. However, it is believed that cages extending deeper into the water, such as those shown in FIGS. 1 and 2, (without forage fish entrances) are more suited to the needs of tadpoles; needs which are quite similar to those of fish. The tadpoles can be transferred to the more shallow cages 86 with platforms when they have changed into frogs.

Figure 8:
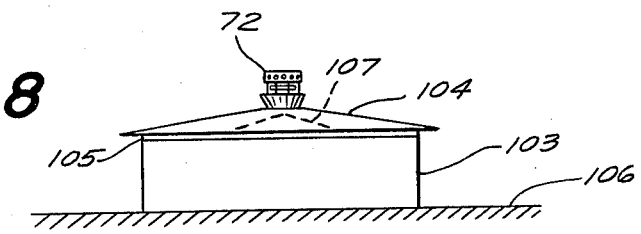
FIG. 8 is an elevation view of another embodiment of the invention.

The feeding of insects to frogs in caged enclosures can be performed on land as well as in floating cages. A land-based frog culture structure 102 is shown in FIG. 8. The structure 102 includes a known circular frog culture tank 103, a roof, and an insect feeder 72 feeding insects into the enclosure formed by the tank 103 and roof 104. A screened ventilation gap 105 is provided between the roof and tank.

The tank 103 includes a peripheral ledge (not shown) and a central water pool with filling and drain conduits, none of which is shown in FIG. 8. The details of tank 103 are shown in U.S. Pat. No. 2,126,056.

Live insects are fed into the enclosure and spread toward the side walls by a conical baffle 107. The frogs catch the insects as they fly near them, or when they fall after colliding with the wall of the tank.

FIG. 8 also illustrates the feeding of insects in the tank culture of fish. In this embodiment, the tank 103 is a conventional fish tank with water supply, drain, aerators, etc., all as are well known. Insects are blown down onto the surface of the water in the tank where they are eaten by the fish in the water.

Figure 9:
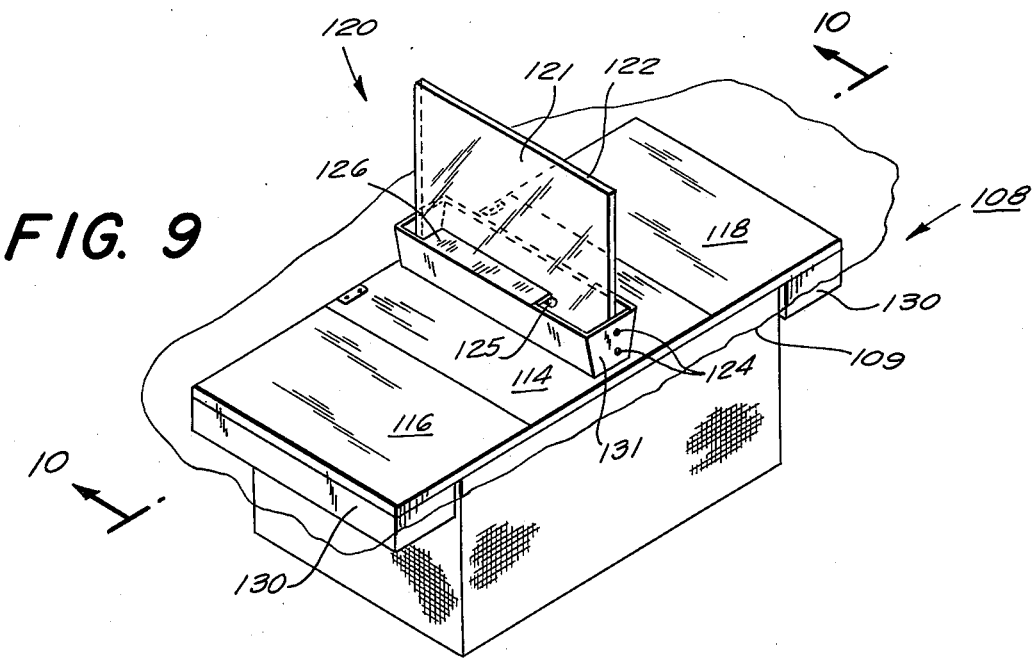
FIG. 9 is a perspective view of an alternative insect trap-feeder of the invention.
Figure 10:
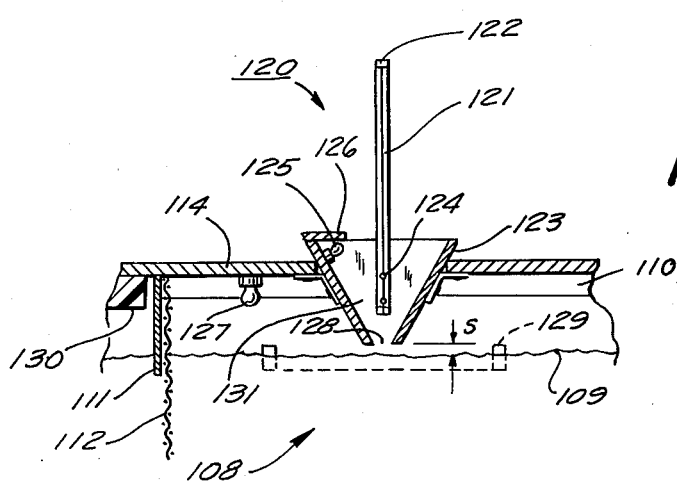
FIG. 10 is a partial cross-sectional view taken alone line 10—10 of FIG. 9.

FIGS. 9 and 10 show a buoyant cage 108 with a static insect collector 102; that is, a collector with no moving parts. The cage has the usual frame 110, "feed-ring" board 111, wire mesh 112, covers 114, 116 and 118, and floats 130.

The collector 120 includes an upstanding translucent barrier screen 121 on a frame 122, an elongated hopper 123 below the screen, and a linear "blacklight" 125 with a transparent cover 126. The lamp is mounted on a sloping side of the hopper wall so that it shines light on the screen. The hopper extends down into the airspace in the cage, and has a restricted lower opening 128 which is positioned a small distance S above the water line 109 in the cage. The hopper has end panels 131, and the frame 122 is fastened to the end panels by means of screw fasteners 124. If necessary, a white lamp 127 is mounted in the cage to induce feeding by fish in the cage. The screen preferably is light in color and has a smooth exterior finish. A white bedsheet or white vinyl sheet are suitable.

Insects are attracted towards the screen 121 and collide with it. The larger insects fall downwardly, are caught in the hopper, and fall through the exit 128 and into the water below where they can be eaten. They cannot easily escape through the opening 128 because it is relatively small, and because it is close to the water surface 109. Thus, even if the insect escapes being eaten immediately, he is trapped in the air space of the cage. The translucency of the screen 121 attracts insects to both of its sides.

The insect collector 20 has the advantage that it needs no fan. Furthermore, the screen provides a relatively large collection area.

If frogs are to be raised in the cage 108, the frog support platform 129 (shown in dashed lines) is located directly under the hopper exit 128, but by a distance "S" which is somewhat larger than when fish are being raised. The reason is that the frogs need room to sit, and also because the frogs should be effective in catching the insects in the air and thus improving the holding effectiveness of the collector 120 without the necessity of feeding all of the insects into the water.

The above-described device and method for attracting forage animals and trapping them in the enclosures in which other aquatic animals are being raised has a number of advantages, in addition to those mentioned above. First, it greatly increases the amount of forage available to the animals being reared. Furthermore, it excludes from the enclosure forage animals too large to be eaten by the enclosed animals, with the result that there is little competition from the forage animals for the food in the enclosure.

The feeding of the animals being reared is greatly simplified if enough of the forage is available to give the animals being raised all they need to eat. If not, the feeding of forage animals can be supplemented by the feeding of insects by means of insect feeders. In this case, additional feeding labor is not needed because the forage animals are attracted into the enclosure by the insects which are attracted and caught by electric lights and fans which can be operated automatically each night by means of timers. Of course, such natural food can be supplemented by the use of commercial pellets, and other known artificial foods.

The above description of the invention is intended to be illustrative and not limiting. Various changes or modifications in the embodiments described may occur to those skilled in the art and these can be made without departing from the spirit or scope of the invention.

I claim:

1. A device for feeding amphibious animals, said device comprising a cage for enclosing said animals, cage support means secured to said cage for supporting said cage with its lower portion immersed in a body of water and its upper portion extending out of the water, a cover on said cage, said cover and said upper portion of said cage forming an enclosure, animal support means mounted on the inside of said cage within said enclosure for providing a rest surface adjacent the surface of said water for said amphibious animals to rest upon, insect feeding means mounted on said cage for attracting and urging insects into said enclosure, said cage and said cover being adapted to prevent the escape of said insects from said enclosure.

2. A device as in claim 1 in which said insect feeding means includes a housing, a lamp mounted on said housing, a fan mounted in said housing, said housing being mounted on said cage for urging said insects into said enclosure.

3. A device as in claim 1 in which said cage support means includes flotation means secured to said cage and enabling it to float on the surface of a body of water.

4. A device as in claim 3 in which said animal support means includes a foraminous structure, cross-members mounted in said cage, said foraminous structure being mounted substantially horizontally on said cross-members, said flotation means also being secured to said cross-members.

5. A method of frog culture comprising the steps of enclosing said frogs in a cage, partially immersing said cage in water, providing a support in said cage for said frogs to sit upon out of the water, and trapping flying insects in said cage with said frogs.

6. A method as in claim 5 including shining light from a lamp into the air and towards the water in said cage, and urging insects towards said cage with airdrafts from a fan.

7. A method as in claim 5 including the step of floating said cage on the surface of a body of water by means of flotation means.

8. A method as in claim 7 including the step of trapping forage aquatic animals from said water in said cage in order to be eaten by said frogs.

* * * * *